US012277094B1

(12) United States Patent
Mortensen et al.

(10) Patent No.: US 12,277,094 B1
(45) Date of Patent: Apr. 15, 2025

(54) SYSTEMS AND METHODS FOR REVISION CONTROL OF AN ELECTRONIC FILE OF A REPOSITORY

(71) Applicant: Veeva Systems Inc., Pleasanton, CA (US)

(72) Inventors: Marius K. Mortensen, Burlington (CA); Eric Mitchell Woolven, Toronto (CA); Abigail Christine Williams, Veldhoven (NL)

(73) Assignee: Veeva Systems Inc., Pleasanton, CA (US)

( * ) Notice: Subject to any disclaimer, the term of this patent is extended or adjusted under 35 U.S.C. 154(b) by 0 days.

(21) Appl. No.: 18/511,194

(22) Filed: Nov. 16, 2023

Related U.S. Application Data

(60) Provisional application No. 63/386,239, filed on Dec. 6, 2022.

(51) Int. Cl.
*G06F 16/00* (2019.01)
*G06F 16/17* (2019.01)
*G06F 16/18* (2019.01)
*G16H 70/20* (2018.01)

(52) U.S. Cl.
CPC ...... *G06F 16/1873* (2019.01); *G06F 16/1734* (2019.01); *G16H 70/20* (2018.01)

(58) Field of Classification Search
CPC .. G06F 16/1873; G06F 16/1734; G16H 70/20
See application file for complete search history.

(56) References Cited

U.S. PATENT DOCUMENTS

| 8,082,277 | B1 * | 12/2011 | O'Brien | G06Q 10/101 |
| | | | | 707/758 |
| 2006/0271839 | A1 * | 11/2006 | Gottlieb | G06F 16/9566 |
| | | | | 707/E17.115 |
| 2015/0248384 | A1 * | 9/2015 | Luo | H04L 51/04 |
| | | | | 715/229 |
| 2016/0110316 | A1 * | 4/2016 | Carter | G06F 40/166 |
| | | | | 715/273 |
| 2017/0076107 | A1 * | 3/2017 | Sundaram | G06F 16/93 |
| 2017/0344596 | A1 * | 11/2017 | Fuller | G06F 16/2358 |
| 2022/0066999 | A1 * | 3/2022 | Lane | G06F 16/168 |

* cited by examiner

*Primary Examiner* — Syed H Hasan

(57) ABSTRACT

A method for revision control of an electronic file including receiving a request to merge a new section of the electronic file with a current section of the electronic file. The method further includes selecting the electronic file based on the request. The electronic file includes multiple sections; each including a revision log including at least one revision log entry data object. The method further includes generating a versioned section. The method further includes generating a revision log entry data object based on the request and the versioned section of the electronic file. The method further includes adding the revision log entry data object to the revision log of the versioned section. The method includes generating an electronic revision log document by compiling at least a portion of each revision log entry data object by date. The method further includes adding the electronic revision log document to the electronic file.

20 Claims, 7 Drawing Sheets

400

☆ ▼ EU PSMF Binder (v4.0) (Approved)

EU PSMF Binder

[All Documents ▼]

[Search Current Binder 🔍]

- 📄 Cover Page (1) (Approved, v1.0) 📄 — 404
- 📄 Table of Contents (Approved, v1.0) 📄 — 406
- ▶ ☐ Core — 408
- ▼ ☐ Annexes — 410
  - ▶ ☐ Annex A: Qualified Person Responsible for Pharmacovigilance — 412
  - ▶ ☐ Annex B: The Organizational Structure of the MAH — 414
  - ▶ ☐ Annex C: Sources of Safety Data — 416
  - ▶ ☐ Annex D: Computerized Systems and Databases — 418
  - ▶ ☐ Annex E: Pharmacovigilance Process, and written procedures — 420
  - ▶ ☐ Annex F: Pharmacovigilance System Performance — 424
  - ▶ ☐ Annex G: Quality System — 426
  - ▶ ☐ Annex H: Products — 428
  - ▶ ☐ Annex I: Document and Record Control — 430
    - ▼ ☐ Change Control, Logbook, Versions and Archive — 432
    - 434 — 📄 EU PSMF Logbook (Draft, v0.1) 📄 ☆ 👤 ⋯
  - ▶ ☐ Annex J: Other Annex Documents — 436
- 📄 Signature Page - EU PSMF

438

440 —

EU PSMF Logbook (v0.1)

EU PSMF Logbook (v0.1) ↗
(Draft)
VV-00023 - EU PSMF Logbook
Pharmacovigilance System Master File (PSMF)
Structure > PSMF Logbook
👤 Last modified by Eric Woolven
4 days ago

PSMF Logbook: LOG-000002 (Active) — 504

▼ Details

- Name LOG-000002 — 506
- Status Active — 508
- Created By John Smith — 510
- Created Date 12 May 2022 4:06 PM EDT — 512
- Last Modified By System — 514
- Last Modified Date 12 May 2022 4:32 PM EDT — 516
- Document Section 2: The Organizational Structure of the MAH (v1.0) — 518

▼ Entries — 520

+ Create    🔍 Show in Tab    1-3 of 3

| Name ▲ | Date | Person Making Change | Summary of Changes |
|---|---|---|---|
| ENTRY-000013 — 524 | 12 May 2018 — 526 | John Smith — 528 | Acquisition of Acme Pharma — 530 |
| ENTRY-000014 — 524 | 02 Jan 2020 — 526 | John Smith — 528 | Brexit implications on QPPV structure — 530 |
| ENTRY-000017 — 524 | 13 May 2022 — 526 | John Smith — 528 | This is new changes that I made on May 13 — 530 |

522

Details / Entries (3)

| Document Name | Entry Date | Person Making Entry | Summary of Changes |
|---|---|---|---|
| Section 4: Computerized Systems and Databases (v0.1) | 16 Jul 2015 | Jane Doe | Migration.... |
| Section 4: Computerized Systems and Databases (v0.1) | 16 Nov 2017 | Jane Doe | Disaster.... |
| Section 2: The Organizational Structure of the MAH (v0.1) | 12 May 2018 | John Smith | Acquisition.... |
| Section 5: Pharmacovigilance Processes and Written Procedures (v0.1) | 09 May 2019 | Jane Doe | Updated.... |
| Section 1: Qualified Person Responsible for Pharmacovigilance (v0.1) | 01 Jan 2020 | Jane Doe | Updated.... |
| Section 2: The Organizational Structure of the MAH (v0.1) | 02 Jan 2020 | John Smith | Brexit.... |
| Section 4: Computerized Systems and Databases (v0.1) | 09 Mar 2021 | Jane Doe | Added.... |
| Section 7: Quality System (v0.1) | 10 Mar 2021 | John Smith | Updated.... |
| Section 3: Sources of Safety Data (v0.1) | 05 Apr 2021 | Jane Doe | Periodic.... |
| Section 6: Pharmacovigilance System Performance (v0.1) | 23 Apr 2021 | Jane Doe | Benchmark.... |
| Section 7: Quality System (v0.1) | 03 Sep 2021 | Jane Doe | Reviewed.... |
| Section 1: Qualified Person Responsible for Pharmacovigilance (v0.1) | 01 Jan 2022 | John Smith | Updated.... |
| Section 5: Pharmacovigilance Processes and Written Procedures (v0.1) | 09 Mar 2022 | Jane Doe | Impacts.... |
| Section 3: Sources of Safety Data (v0.1) | 05 Apr 2022 | Jane Doe | Updated.... |
| Section 6: Pharmacovigilance System Performance (v0.1) | 02 May 2022 | Jane Doe | Benchmark.... |
| Section 7: Quality System (v0.1) | 12 May 2022 | John Smith | Added.... |
| Table of Contents (v0.1) | | | |
| Cover Page (1) (v0.1) | | | |

EU PSMF Logbook (v0.1) Draft

Logbook Export Date: 12 May 2022 4:19 PM EDT

| Document Name | Entry Date | Person Making Entry | Summary of Changes |
|---|---|---|---|
| Section 4: Computerized Systems and Databases (v0.1) | 16 Jul 2015 | Jane Doe | Migration to AWS |
| Section 4: Computerized Systems and Databases (v0.1) | 16 Nov 2017 | Jane Doe | Disaster recovery plan update |
| Section 2: The Organizational Structure of the MAH (v0.1) | 12 May 2018 | John Smith | Acquisition of Acme Pharma |
| Section 5: Pharmacovigilance Processes and Written Procedures (v0.1) | 09 May 2019 | Jane Doe | Updated based on new GDPR regulation |
| Section 1: Qualified Person Responsible for Pharmacovigilance (v0.1) | 01 Jan 2020 | Jane Doe | Updated QPPV certificates and responsibilities |
| Section 2: The Organizational Structure of the MAH (v0.1) | 02 Jan 2020 | John Smith | Brexit implications on QPPV structure |
| Section 4: Computerized Systems and Databases (v0.1) | 09 Mar 2021 | Jane Doe | Added auto scaling and load balancing |
| Section 7: Quality System (v0.1) | 10 Mar 2021 | John Smith | Updated to meet new regulation around quality systems |
| Section 3: Sources of Safety Data (v0.1) | 05 Apr 2021 | Jane Doe | Periodic Review |
| Section 6: Pharmacovigilance System Performance (v0.1) | 23 Apr 2021 | Jane Doe | Benchmark testing |
| Section 7: Quality System (v0.1) | 03 Sep 2021 | Jane Doe | Reviewed for changes. None needed |
| Section 1: Qualified Person Responsible for Pharmacovigilance (v0.1) | 01 Jan 2022 | John Smith | Updated QPPV certificates |
| Section 5: Pharmacovigilance Processes and Written Procedures (v0.1) | 09 Mar 2022 | John Smith | Impacts of privacy shield |
| Section 3: Sources of Safety Data (v0.1) | 05 Apr 2022 | Jane Doe | Updated to reflect adding Vault Safety Signal as a signal management tool |
| Section 6: Pharmacovigilance System Performance (v0.1) | 02 May 2022 | Jane Doe | Benchmark testing |
| Section 7: Quality System (v0.1) | 12 May 2022 | Jane Doe | Added section about Vault SafetyDocs |
| Table of Contents (v0.1) | | Jane Doe | |
| Cover Page (1) (v0.1) | | John Smith | |

0 Comments

SYSTEMS AND METHODS FOR REVISION CONTROL OF AN ELECTRONIC FILE OF A REPOSITORY

CROSS-REFERENCE TO RELATED APPLICATIONS

This application claims priority to U.S. Provisional Patent Application No. 63/386,239, filed Dec. 6, 2022, which is incorporated herein by reference in its entirety.

TECHNICAL FIELD

The present disclosure relates to systems and methods for revision control of electronic files of repositories.

BACKGROUND

Researchers, scientists, industry players, academics, government regulators, and other stakeholders are increasingly in need of ways to track and control revisions in electronic pharmacovigilance safety master files (PSMFs).

SUMMARY

One embodiment relates to a method for revision control of an electronic file. The method includes receiving a request to merge a new section of the electronic file with a current section of the electronic file. The request includes an electronic document associated with the new section of the electronic file. The method further includes selecting the electronic file from a repository of the provider computing system based on the request. The electronic file includes multiple sections including the current section. Each section of the multiple sections includes a revision log including at least one revision log entry data object. Each revision log entry data object includes a date. The method further includes generating a versioned section of the electronic file based on the request. The versioned section includes the electronic document of the request and the revision log of the current section. The method further includes generating a revision log entry data object based on the request and the versioned section of the electronic file. The revision log entry data object includes a new date. The method further includes adding the revision log entry data object to the revision log of the versioned section. The method further includes generating an electronic revision log document by compiling at least a portion of each revision log entry data object of each revision log of each section of the multiple sections by date. The method further includes adding the electronic revision log document to the electronic file, and storing the electronic file in the repository.

Another embodiment relates to a method for revision control of an electronic file. The method includes receiving a request to merge a new section of the electronic file with a current section of the electronic file. The request includes an electronic document associated with the new section of the electronic file. The method further includes selecting the electronic file from a repository of the provider computing system based on the request. The electronic file includes the current section. The current section includes a revision log including a first revision log entry data object. The first revision log entry data object includes a date. The method further includes generating a versioned section of the electronic file based on the request. The versioned section includes the electronic document of the request and the revision log of the current section. The method further includes generating a second revision log entry data object based on the request and the versioned section of the electronic file. The second revision log entry data object includes a new date. The method further includes adding the second revision log entry data object to the revision log of the versioned section. The method further includes generating an electronic revision log document by compiling at least a portion of the first revision log entry data object and the second revision log entry data object of the revision log by date. The method further includes adding the electronic revision log document to the electronic file, and storing the electronic file in the repository.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIG. 4 is an illustration of some aspects of a user interface generated by the revision control system of FIG. 1 to manage a PSMF, according to an example embodiment.

FIG. 5 is an illustration of some aspects of a user interface generated by the revision control system of FIG. 1 to manage an electronic revision log, according to an example embodiment.

FIG. 6 is an illustration of some aspects of an electronic PSMF document generated by the revision control system of FIG. 1, according to an example embodiment.

FIG. 7 is an illustration of some aspects of an electronic revision log document generated by the revision control system of FIG. 1, according to an example embodiment.

DETAILED DESCRIPTION

Figure 1:
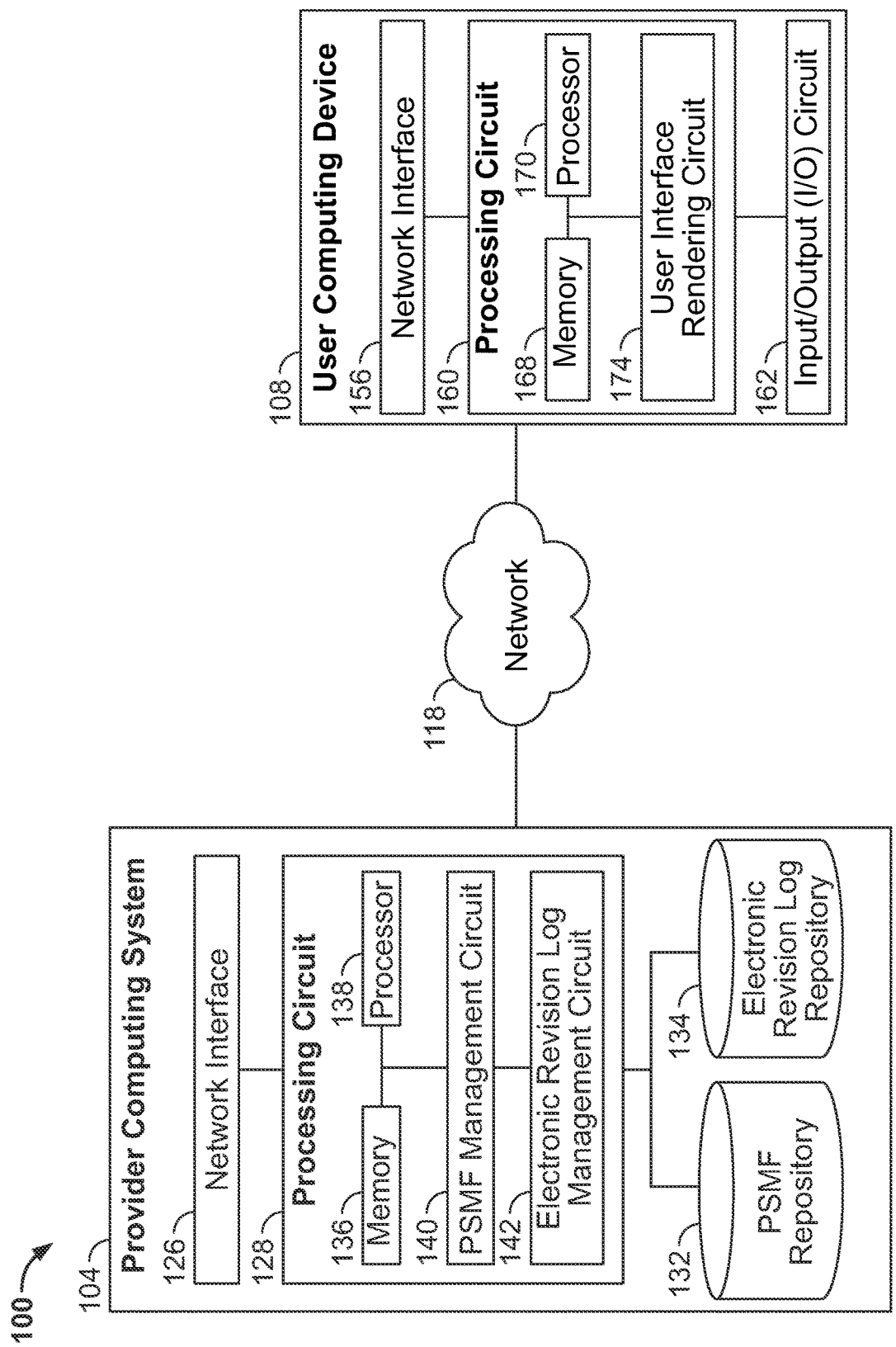
FIG. 1 is a component diagram of a revision control system, according to an example embodiment.

Referring generally to the figures, systems and methods for revision control in a PSMF are disclosed. The systems and methods described herein provide for a multi-accessible electronic revision log, which provides for improved quality and ease-of-use of the electronic revision log, thereby helping and improving the pharmacovigilance industry by more accurately tracking revisions in a PSMF. For example, by generating a revision log entry data object, in response to receiving a request to merge a new section of the PSMF with a current section of the PSMF, and then adding the revision log entry data object to the electronic revision log, the present systems and methods allow for multiple users to add entries to the electronic revision control log at the same time. In comparison, typical PSMF revision control systems typically only allow a single user to add entries to the electronic revision log by checking the revision log out and then checking the revision log back in after the changes are made. As a result, the present systems and methods can more quickly and accurately capture the revision made to the sections of the PSMF in the revision control log, which provides for a better standardized and more accurate PSMF overall. For instance, the present system and methods capture all revisions to the PSMF in the revision control log, at the time they happened, as compared to at a later date or time (when portions of the revisions may be forgotten) due to the electronic revision control log being checked-out. As a result, the present systems and methods provide a technical solution to the problem of multi-accessible revision control systems.

Additionally, because the systems and methods described herein automatically generate the revision log entry data objects and add the data objects to the electronic revision log, the systems and methods described herein require less processing power and memory than typical PSMF revision control systems. For example, in typical revision control systems, users must make changes to the section of the PSMF and provide the revised section for storage therein. Further, users must then make changes to the revision log and provide the revised revision log for storage therein. In comparison, the present systems and methods receive the request to modify the current section of the PSMF including the new section of the PSMF and the summary of the changes. The present systems and methods then generate the revision log entry data object and add the revision log entry data object to the electronic revision log. As a result, the present systems and methods require less communication between computing devices than in typical PSMF revision control systems, thereby using less processing power to communicate and memory to store the communications.

Moreover, because the systems and methods described herein generate an electronic revision log for each section of the PSMF, the electronic revision log may be reused in multiple PSMFs and then combined to generate the electronic revision log document. For instance, a PSMF for (associated with) Japan and a PSMF for (associated with) the EMA may both reuse the same Global Section such as the Core Section D: Computerized Systems and Databases, because the Pharmacovigilance systems in Japan and the EMA utilize the same Computerized Systems and Databases. In this regard, if a revision is made to the Core Section D, the revisions may be stored in the electronic revision log associated with the Core Section D. Then, the revisions may be automatically captured in the PSMF for Japan and the PMSF for the EMA. In comparison, typical PSMF revision control systems typically require a user to enter the same revisions in a logbook of the PMSF for Japan and in a logbook of the PSMF for the EMA, thereby requiring twice the work, processing power, and memory as compared to the present systems and methods.

In an illustrative scenario, a provider computing system may receive a request to generate a PSMF; the request may include one or more sections of the PSMF and/or identify one or more global sections that are to be included in the PSMF. Next, the provider computing system may generate an electronic revision log associated with each of the received sections of the PSMF; and/or retrieve the identified sections of the PSMF from a PSMF repository and the associated electronic revision logs from an electronic revision log repository. Next, the provider computing system may generate a revision log entry data object for each received section of the PSMF. In some embodiments, the revision log entry data object may include a standard or preset entry for the first revision log entry data object for each respective electronic revision log. Next, the provider computing system may add each revision log entry data object to the respective electronic revision log. Next, the provider computing system may generate the PSMF including the one or more sections of the PSMF and each electronic revision log. In some embodiments, to generate the PSMF, the provider computing system may generate a PSMF data object including a reference pointer or link to each section of the PSMF. Next, the provider computing system may store the PSMF in a PSMF repository. In some embodiments, the provider computing system may store each of the electronic revision logs and each of the sections of the PSMF in a repository.

As used herein, the term "Pharmacovigilance Safety Master File" or "PSMF" (also referred to as an electronic file) can include a detailed description of the pharmacovigilance system used by a company (or drug registration) with respect to one or more authorized medicinal products. In this regard, the "Pharmacovigilance Safety Master File" or "PSMF" can include a Pharmacovigilance Safety Master File as defined by the EMA, the ISO, the WHO, the FDA, or other national health agencies governing PSMFs. Further, the "Sections" or "Portions" of the "PSMF" can include the one or more sections or electronic documents that make up the detailed description such as a cover page, a table of contents, a Qualified Person Responsible for Pharmacovigilance Section, a Sources of Safety Data Section, a Logbook of changes or revisions, and other sections identified as being included in a PSMF by the EMA (e.g., in the Commission Implementing Regulation (EU) No 520/2012), the ISO, the WHO, the FDA, or other national health agencies governing PSMFs.

Additionally, each "Pharmacovigilance Safety Master File" or "PSMF" can include an electronic document or document file (e.g., a Word® document file (DOC/DOCX), an Excel® document file (XLS), a PDF document file, a TXT document file, and the like); a data object (e.g., a PSMF data object) including the sections and revision log (and data objects) of the PSMF described herein; and/or an electronic file binder. Likewise, each "section" of the "PSMF" can include an electronic document or file and/or a data object (e.g., a specific section data object) including the data of the specific section described herein. For instance, a specific section (e.g., Appendix A) may include a data object that represents the section and has multiple fields (e.g., a name field, a description field, a parent PSMF data object, a child revision log data object, etc.) and an electronic document or file. Similarly, each "electronic revision log" or "revision log" can include an electronic document file and/or a data object (e.g., an electronic revision log data object) including the data of the electronic revision log. For instance, a specific revision log (e.g., Appendix A) may include a data object that represents the revision log and has multiple fields (e.g., a name field, a description field, a parent section data object, multiple child revision log data entry objects, etc.) and an electronic document or file.

As used herein, the terms "information" and "data" may be used interchangeably such that one may be substituted for the other and vice versa.

Referring now to FIG. 1, a system 100 for revision control in a PSMF is shown, according to an example embodiment. The system 100 includes a provider computing system 104 and one or more user computing devices 108 connected by a secure network (e.g., a network 118). In some embodiments, the system 100 further includes one or more health agency computing systems (not shown) each associated with a health agency (e.g., the FDA, the EMA, the WHO, etc.).

The network 118 communicably and operably couples the provider computing system 104 and the user computing devices 108 such that communicable and operable computing may be provided between the provider computing system 104 and the user computing devices 108 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (Saas) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to each of the user computing devices 108 over the network 118 in response to authenticating the respective user computing device 108. As shown, the provider computing system 104 may include a network interface 126, a processing circuit 128, an electronic revision log repository 134, and a PSMF repository 132. In some embodiments, the provider computing system 104 may include an input/output circuit (e.g., similar to or the same as an input/output circuit 162 that will be described further herein).

The network interface 126 is structured to establish connections with the user computing devices 108 by way of the network 118. The network interface 126 includes program logic and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

The processing circuit 128, as shown, comprises a memory 136, a processor 138, a PSMF management circuit 140, and an electronic revision log management circuit. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 138 to control the processing circuit 128. The memory 136 may be or include tangible, non-transient volatile memory and/or non-volatile memory. The processor 138 may be implemented as a general-purpose processor, an application specific integrated circuit (ASIC), one or more field programmable gate arrays (FPGAs), a digital signal processor (DSP), a group of processing components, or other suitable electronic processing components.

The PSMF management circuit 140 is structured or configured to generate, modify, and store a PSMF. For example, the PSMF management circuit 140 may receive request to generate a PSMF from the user computing device 108. The request may include one or more sections of the PSMF. In response, the PSMF management circuit 140 generate the PSMF (and a data object representing the PSMF) including the sections of the PSMF and store the newly generated PSMF (and corresponding sections) within the PSMF repository 132. Further, the PSMF management circuit 140 may indicate the generation of the PSMF (and the addition of the received sections) to the electronic revision log management circuit 142 for recording of the revisions to the PSMF and generation of an Electronic Revision Log (due to the new generation of the PSMF). In some embodiments, the PSMF management circuit 140 may further generate and store version information associated with the newly generated PSMF (e.g., version 1.0) within the PSMF repository 132. In another example, the PSMF management circuit 140 may receive a request to modify the PSMF. The request may identify a specific current section of the PSMF and include a new section that is to be merged with or replace the current section. In response, the PSMF management circuit 140 may select the PSMF from the PSMF repository 132 and combine the new section of the PSMF with the current section of the PSMF, thereby generating a versioned section of the PSMF. Further, the PSMF management circuit 140 may indicate or provide the revisions to the section of the PSMF to the electronic revision log management circuit 142 for recording of the revisions to the PSMF. The PSMF management circuit 140 may store the PSMF including the versioned section of the PSMF within the PSMF repository 132. In some embodiments, the PSMF management circuit 140 may further generate and store version information associated with the PSMF (e.g., version 2.0) within the PSMF repository 132.

The electronic revision log management circuit 142 is structured or configured to generate, modify, and store an electronic revision log (also referred to as a logbook) and associated electronic revision log entry data objects (also referred to as logbook entry data objects). For instance, the electronic revision log management circuit 142 may receive a request or indication that a Section of the PSMF was newly generated. In response, the electronic revision log management circuit 142 may generate an electronic revision log associated with the PSMF. The electronic revision log may store the revisions that are made to the PSMF. Further, the electronic revision log management circuit 142 may generate a revision log entry data object including the previous version of the section, a reference pointer or link to the current version of the section, the new version of the section, the date and/or time the change was made, and a text summary of the revisions (e.g., "Initial Creation of Section X"). Then, the electronic revision log management circuit 142 may add the newly generated revision log entry data object within the newly generated electronic revision log and store the electronic revision log within the electronic revision log repository 134.

The PSMF repository 132 is a repository (e.g., a database, cloud storage, etc.) that is structured or configured to receive, store, and manage (i.e., select and return) one or more PSMFs (e.g., the PSMF data object and/or the Electronic PSMF document) and their associated sections. (e.g., each section's data object and/or the electronic document associated with each section). For example, the PSMF repository 132 may receive a PSMF (including the PSMF data object and the Electronic PSMF document) and the one or more sections of the PSMF (including the respective sections' data object and the electronic document associated with each section) and store the PSMF including the one or more sections therein. Further, the PSMF repository 132 may receive a request or query identifying a specific PSMF (or sections thereof) and return the PSMF. In this regard, the PSMF repository 132 can be structured according to various database types, such as relational, hierarchical, network, flat, point-in time, and/or object relational. In some embodiments, the PSMF repository 132 includes a plurality of nonvolatile/non-transitory storage media such as solid-state storage media, hard disk storage media, virtual storage media, cloud-based storage drives, storage servers, and/or the like.

Likewise, the electronic revision log repository 134 is a repository (e.g., a database, cloud storage, etc.) that is structured or configured to receive, store, and manage one or more electronic revision logs and their associated revision log entry data objects. For example, the electronic revision log repository 134 may receive an electronic revision log (e.g., the revision log data object and/or the electronic revision log document) including multiple revision log entry data objects and store the electronic revision log therein. Further, the electronic revision log repository 134 may receive a request or query identifying a specific electronic revision log and return the electronic revision log. In this regard, the electronic revision log repository 134 can be structured according to various database types, such as relational, hierarchical, network, flat, point-in time, and/or object relational. In some embodiments, the electronic revision log repository 134 includes a plurality of nonvolatile/non-transitory storage media such as solid-state storage media, hard disk storage media, virtual storage media, cloud-based storage drives, storage servers, and/or the like. In some embodiments, the electronic revision log repository 134 and the PSMF repository 132 are the same repository, and each electronic revision log is stored within the corresponding PSMF. For instance, the electronic revision log (and multiple revision log entry data objects) may be included within the corresponding PSMF and stored within the PSMF repository 132.

In some embodiments, each different data or information type (e.g., each section of the PSMF, the electronic revision log, etc.) may be stored in, and the provider computing system 104 may include a separate repository for each (not shown). For example, the provider computing system 104 may include a separate repository for each section of the PSMF (e.g., a table of contents repository, a products section repository, etc.). In this regard, the PSMF may be a file binder that includes a reference pointer or link to each corresponding section of the PSMF and the electronic revision log which can then (e.g., when requested) be output as a single document or file. Each repository may be similar to or structured the same as the PSMF repository 132. In some embodiments, each section of the PSMF may be stored in the same repository (e.g., a PSMF Section Repository (not shown), which is separate from the PSMF repository 132 and/or the electronic revision log repository 134).

Still referring to FIG. 1, each of the one or more user computing devices 108 can be any type of computing device or computing system. For instance, each of the user computing devices 108 can be one or more of a mobile phone, a tablet computer, a laptop computer, a smart watch, a server computer system, or any other internet-connected device. In operation, the user computing devices 108 may communicate and interface with the provider computing system 104 via the network 118 to make one or more revisions to the PSMF (e.g., to one or more sections of the PSMF). As shown, the user computing device 108 may include a network interface 156, a processing circuit 160, and the input/output (I/O) circuit 162.

The network interface 156 is structured to establish connections with the provider computing system 104 by way of the network 118. The network interface 156 includes program logic and/or hardware-based components that connect the user computing device 108 to the network 118. For example, the network interface 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 156 includes the hardware and machine-readable media structured to support communication over multiple channels of data communication (e.g., wireless, Bluetooth, near-field communication (NFC). In some embodiments, the network interface 156 includes cryptography logic and capabilities to establish a secure communications session.

The processing circuit 160, as shown, comprises a memory 168, a processor 170, and a user interface generation or rendering circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate arrays (FPGAs), a digital signal processor (DSP), a group of processing components, or other suitable electronic processing components.

The user interface generation or rendering circuit 174 may be configured to receive a user interface (e.g., a web interface in an HTML file and related files, a downloaded graphical user interface, etc.) from the provider computing system 104 and render the user interface on the user computing device 108 via the I/O circuit 162. In this way, the provider computing system 104 may generate one or more user interfaces and provide the one or more user interfaces to the user interface generation circuit 174 to be rendered and enable display on the user computing device 108 (e.g., on a display of the I/O circuit 162 of the user computing device 108).

The I/O circuit 162 is structured to receive communications from and provide communications to the user of one or more of the user computing devices 108 (e.g., the user). In this regard, the I/O circuit 162 is structured to exchange data with the processing circuit 160 to provide output to the user and to receive input from the user. As a result, the I/O circuit 162 may include a display that may be manipulated by the application. In some embodiments, the I/O circuit 162 may also include a keyboard, a mouse, a joystick, a touch screen, touch areas, soft keys, a microphone, a speaker, a vibration mechanism, a sensor, a RFID scanner, or other input or output devices described herein.

Figure 2:
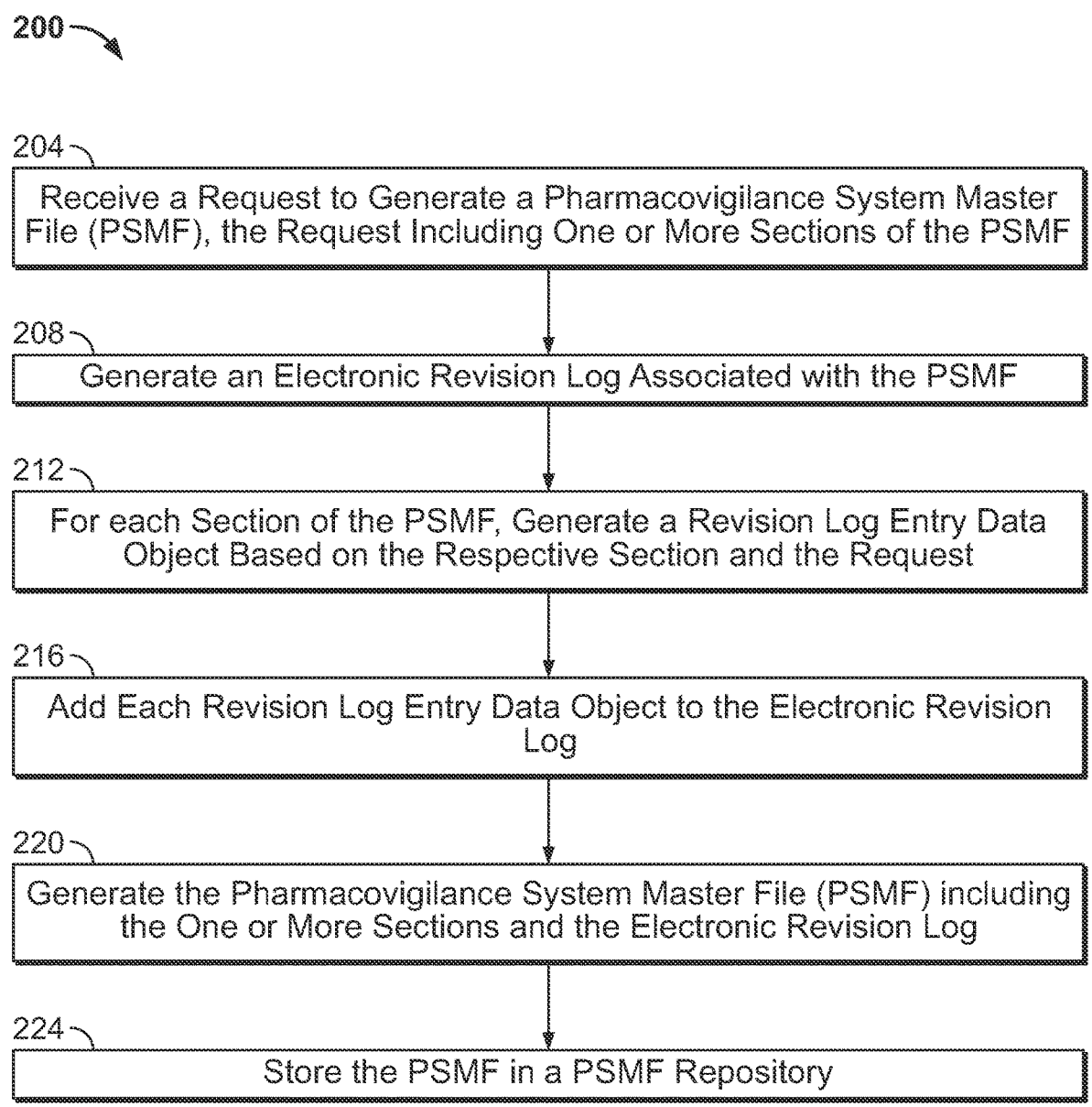
FIG. 2 is a flow diagram of a method for generating a PSMF and electronically tracking revisions, according to an example embodiment.

Referring now to FIG. 2, a method 200 of generating a PSMF and electronically tracking revision in the PSMF is shown, according to an example embodiment. Method 200 can be carried out by the system of FIG. 1. More particularly, the method 200 can be carried out by the processing circuit 128 of the provider computing system 104 and through communication with the one or more user computing devices 108.

Method 200 commences at step 204 at which the provider computing system 104 request to generate a PSMF from one of the user computing devices 108. The request may include one or more sections of the PSMF and a text summary of changes or revisions for each section. In some embodiments, each section of the PSMF and the text summary of revisions may be received separately (e.g., after) the request to generate the PSMF. In some embodiments, the request to generate the PSMF may identify an associated medical product or company with which the PSMF is associated. In some embodiments, the request to generate the PSMF may include a list of permissions and users (e.g., emails, usernames) who are permitted to modify the PSMF.

In some embodiments, if the provider computing system 104 did not receive each (expected) section of the PSMF, the provider computing system 104 may generate a template or placeholder section, in the expected sections place. For instance, the user computing device 108 may provide a request to generate the PSMF including every section of the PSMF but one (e.g., the Quality Systems section). In response, the provider computing system 104 may generate a template section in place of the missing section and use the template section during the method 200 in place of the missing section. In other embodiments, if the provider computing system 104 did not receive each (expected) section of the PSMF, the provider computing system 104 may send a notification to the user computing device 108 indicating as such and wait to proceed with the method 200 until each section of the PSMF is received. In some embodiments, if the provider computing system 104 did not receive each (expected) section of the PSMF, the provider computing system 104 may proceed with the method 200 and fulfill each step of the method 200 with the sections of the PSMF that were received.

In some embodiments, the request to generate the PSMF may include or identify a structure of the PSMF (e.g., one or more core sections and/or annex sections that are to be included in the PSMF) and a region or health authority associated with the PSMF. In this regard, the sections of the PSMF and the PSMF may be modular such that the user of the user computing device 108 can decide what is to be included in the PSMF and what is not to be included in the PSMF. For instance, a PSMF may be specified (in the request to generate the PSMF) to include multiple global sections (e.g., Core Section D: Computerized Systems and Databases) that may be reused in multiple PSMFs (e.g., a first PSMF for Japan and a second PSMF for the USA) and multiple regional sections (e.g., Core Section A: Qualified Person Responsible for Pharmacovigilance, Japan; Core Section H: Products, Japan; etc.) that may be used in one specific region of the world. In this regard, each PSMF (e.g., the PSMF for Japan, the PSMF for the USA, the PSMF for the EMA, etc.) may include slight variations that are specified by the user of the user computing device 108 in the request to generate the PSMF. In some embodiments, the provider computing system 104 may provide a template or framework for the PSMF for each specific health authority or country. For instance, for a PSMF that is to be generated and associated with the EMA, may include the seven cores and annexes shown in FIG. 7 (along with the other structural sections (e.g., Cover page, table of contents, etc.). In this regard, prior to step 204, the provider computing system 104 may provide a template or framework for the PSMF to the user computing device 108 that is specific to the EMA. The user computing device 108 may then customize or modify the specific PSMF for the EMA (e.g., remove sections, add sections, combine sections), and include that specific framework for the PSMF in the request to generate the PSMF. Further, as described herein, because each PSMF may share one or more global sections, the request to generate the PSMF may identify PSMF sections that have previously been generated for another PSMF. For instance, the user computing device 108 may provide a request to generate a PSMF for the EMA that identifies a previously generated global section (e.g., Core Section D: Computerized Systems and Databases, Annex D, etc.). Accordingly, instead of receiving the respective Sections from the user computing device 108, the provider computing system 104 may retrieve the Sections from the PSMF repository 134 or the PSMF Section repository (not shown).

Once the provider computing system 104 has received the request to generate the PSMF, the method 200 proceeds to step 208 at which the provider computing system 104 generates an electronic revision log (also referred to as a revision log) associated with the PSMF. As described herein, the electronic revision log may be a record of the revisions or changes made to the sections of the PSMF. For instance, if a company changes Pharmacovigilance leadership due to regulatory changes (e.g., the United Kingdom's Exit from the EU), the PSMF would be updated (in the Qualified Person Responsible for Pharmacovigilance Section) to indicate as such. Further, the electronic revision log may include a log line indicating the revisions and the text summary of the changes (see FIG. 6). In this regard, each PSMF may include an associated electronic revision log.

In some embodiments, at step 208, the provider computing system 104 may generate an electronic revision log for each section of the PSMF. In this regard, each section of the PSMF may include or be associated with an electronic revision log. For instance, the revision log data object of the revision log may include a reference pointer or link to the current version of the section with which the revision log is associated (e.g., the revision log associated with specific section X of the PSMF includes a reference pointer or link (in the revision log data object) to the current version of specific section X (e.g., to the data object associated of the specific section X). By doing so, the electronic revision logs may be filterable such that the user computing device 108 can specify and review the revision log that is specific to a certain section of the PSMF (see FIG. 5 for an example). Further, by generating an electronic revision log for each section of the PSMF, the electronic revision log may be reused in multiple PSMFs and then combined to generate the electronic revision log document. For instance, using the example above, a PSMF for (associated with) Japan and a PSMF for (associated with) the EMA may both reuse the same Global Section such as the Core Section D: Computerized Systems and Databases, because the Pharmacovigilance systems in Japan and the EMA utilize the same Computerized Systems and Databases. In this regard, if a revision is made to the Core Section D, the revisions may be stored in the electronic revision log associated with the Core Section D. Then, the revisions may be automatically captured in the PSMF for Japan and the PMSF for the EMA. In comparison, typical PSMF revision control systems typically require a user to enter the same revisions in a logbook of the PMSF for Japan and in a logbook of the PSMF for the EMA, thereby requiring twice the work, processing power, and memory as compared to the present systems and methods. In some embodiments, when generating each electronic revision log, the provider computing system 104 may generate each to include a reference pointer or link to the associated or respective section of the PSMF. For instance, the electronic revision log associated with the Section D may be generated to include a reference pointer or link to Section D of the PSMF and vice versa.

In some embodiments, at step 212, the provider computing system 104 may generate version data (e.g., version 0.1 for the generation of the revision log) associated with the revision log (and/or the revision log data object of the revision log). The version data may indicate the version of the revision log and change (e.g., increment) as the revision log is altered and/or approved.

Once the provider computing system 104 has generated the electronic revision log(s), the method 200 proceeds to step 212, at which the provider computing system 104 generates a revision log entry data object for each section of the PSMF. For instance, the request may include a text summary of revisions for each respective section of the PSMF. Accordingly, at step 212, the provider computing system 104 may generate a revision log entry data object, for each section of the PSMF, that includes the respective text summary of revisions, the date and/or time the revisions were received, a record of who made the changes (e.g., the name of the user who made the changes), a new version of the section, and/or a reference pointer or link to the current version of the section.

As described herein, each revision log entry data object represents or constitutes an entry into the electronic revision log. Each revision log entry data object thereby provides details of the revisions that were made to a section of the PSMF in a linear and multi-accessible fashion. In typical PSMF revision control systems, users must individually access the electronic revision log and add entries manually. For instance, a user may make a change to Section 3 of the PSMF. Accordingly, the user must then access the electronic revision log and manually describe the changes made to Section 3. In a typical revision control system, this process is complicated by the fact that the revision log must be manually checked-out, edited, and then checked-in. For instance, if two users are editing the PSMF, and want to add an entry to the electronic revision log at the same time, one user must wait for the other to finish their edits and to check the revision log in. In comparison, the present systems and methods provide for a simple and multi-accessible revision log that utilizes revision log entry data objects that are automatically generated by the systems described herein and added to the electronic revision log. If two users were editing two sections of the PSMF, in the present systems and methods, the provider computing system 104 would automatically generate a revision log entry data object for each, and add the revision log entry data object to the electronic revision log. As a result, neither user would have to wait for one another to check the electronic revision log in. As a result, the present systems and methods provide a technical solution to the problem of multi-accessible revision control systems.

Additionally, because the systems and methods described herein automatically generate the revision log entry data objects and add the data objects to the electronic revision log, the systems and methods described herein require less processing power and memory than typical PSMF revision control systems. For example, in typical revision control systems, users must make changes to the section of the PSMF and provide the revised section for storage therein. Further, users must then make changes to the revision log and provide the revised revision log for storage therein. In comparison, in the present systems and methods, the provider computing system 104 receives the request to modify the current section of the PSMF including the new section of the PSMF and the summary of the changes. The provider computing system 104 then generates the revision log entry data object and adds the revision log entry data object to the electronic revision log. As a result, the present systems and methods communicate with the user computing device 108 less than in typical PSMF revision control systems, thereby using less processing power to communicate and memory to store the communications.

In some embodiments, for the initial entry for each section (e.g., when the section is first received or the PSMF is first generated), the provider computing system 104 may generate a standard text summary of revisions such that the user computing device 108 does not need to provide one. For instance, for each initial entry for each section, the provider computing system 104 may generate or use a template summary of changes (e.g., "initial entry", "first entry" "initial creation", and so on). By doing so, the provider computing system 104 may provide for a simplified initial setup of a PSMF. For instance, because a PSMF has so many sections, it is typical for a PSMF to be created one section at a time. (e.g., create one section then upload one section, create another section then upload the section, and so on). In comparison, the systems and methods described herein (e.g., the method 200) provide a simplified method for generating the PSMF at one time by generating templates for missing sections of the PSMF (or continuing without the unreceived sections) and automatically generating the initial entry for each section. By doing so, the systems and methods described herein require less communication between the user computing device 108 and the provider computing system 104 for the initial setup of the PSMF, and thereby use less processing power to do so. Moreover, by automatically generating the initial entry within the revision log, the systems and methods described herein provide for a standardized initial entry into the logbook of the PSMF, thereby improving the quality of the PSMF and providing for clearer record keeping in a standardized setting.

Once the provider computing system 104 has generated each revision log entry data object, the method 200 proceeds to step 216 at which the provider computing system 104 adds each revision log entry data object to the respective electronic revision log(s). For instance, the provider computing system 104 may add a reference pointer or link (e.g., within the electronic revision log data object) to each revision log entry data object at step 216. In another example, the provider computing system 104 may add the data included within each revision log entry data object to the electronic revision log. In some embodiments, step 208 occurs after step 212, and the provider computing system 104 generates the electronic revision log and adds the revision log entry data objects to the electronic revision log directly after generating the electronic revision log. If, at step 212, the provider computing system 104 generates an electronic revision log for each section of the PSMF, at step 216, the provider computing system 104 may add each revision log entry data object to the respective electronic revision log. For instance, an electronic revision log entry data object that is associated with Section A of the PSMF may be added to the electronic revision log associated with Section A of the PSMF, and so on.

In some embodiments, after step 216 or step 208, the provider computing system 104 may generate an electronic revision log document. The electronic revision log document may be a PDF, HTML/HTMLS, XLS, TXT, or DOC/DOCX file that includes each of the revision log entries of each of the revision logs within a single electronic document. To do so, the provider computing system 104 may compile each revision log entry data object from each electronic revision log into the same file format in the correct order displayed (e.g., an entry from 2001 is before an entry from 2002, etc.). For instance, the PSMF may include ten sections with each section having a revision log for storing revision information. Accordingly, after step 216 or 208, the provider computing system 104 may select each of the revision log entries of each revision log and compile or merge them by date. In some embodiments, the electronic revision log document may be stored with the electronic revision log in the electronic revision log repository 134. FIG. 7 shows an example electronic revision log document.

Once the provider computing system 104 has added each revision log entry data object to the electronic revision log, the method 200 proceeds to step 220 at which the provider computing system 104 generates the PSMF including the one or more sections of the PSMF and the electronic revision log. For instance, to add the one or more sections of the PSMF and the electronic revision log to the PSMF, the provider computing system 104 may add a reference pointer or link within the PSMF (e.g., within the PSMF data object) to the data objects associated with each of the sections of the PSMF and the data object associated with the electronic revision log. In another example, the provider computing system 104 may add the electronic documents associated with the each of the sections of the PSMF and the electronic revision log to the PSMF. If, at step 212, the provider computing system 104 generates an electronic revision log for each section of the PSMF, at step 220, the provider computing system 104 may add each electronic revision log to the PSMF (e.g., a reference pointer or link to each electronic revision log). In other embodiments, each section of the PSMF may include a pointer or link to the respective electronic revision log, and therefore the PSMF only includes a reference pointer or link to each of the sections of the PSMF. In some embodiments, at step 220, the provider computing system 104 may add the electronic revision log to the PSMF by including a reference pointer or link in the PSMF to the electronic revision log document described herein.

Once the provider computing system 104 has generated the PSMF, the method 200 proceeds to step 224 at which the provider computing system 104 stores the PSMF within the PSMF repository 132. In some embodiments, the PSMF may be stored separately from the sections of the PSMF and/or the electronic revision log. For instance, the PSMF may be stored within the PSMF repository 132, the electronic revision log may be stored within the electronic revision log repository 134, and the other sections of the PSMF may be stored in separate repositories (as described herein). Accordingly, at step 220 when the PSMF is generated including the one or more sections of the PSMF and the electronic revision log, the provider computing system 104 may generate the PSMF to include a reference pointer or link to each of the one or more sections and the electronic revision log. In this regard, the PSMF may include a reference pointer or link to the current versions of the one or more sections and the electronic revision log. In this regard, at step 224, the provider computing system 104 may store each of the sections of the PSMF within the PSMF Section Repository (not shown) described herein and the PSMF in the PSMF repository 132.

In some embodiments, before step 224, the provider computing system 104 may generate an electronic PSMF document. The electronic PSMF document may be a PDF, HTML/HTMLS, XLS, TXT, or DOC/DOCX file that includes each of the sections of the PSMF and the electronic revision log within a single electronic document. To do so, the provider computing system 104 may generate a table of contents representative of each section and the electronic revision log and then compile each section of the PSMF into the same file format in the correct order displayed (e.g., section 1 before section 2, etc.). In some embodiments, the electronic PSMF document may be stored with the PSMF in the PSMF repository 132 at step 224. FIG. 6 shows an example electronic PSMF document. In some embodiments, after step 224, the provider computing system 104 may receive a request to output the PSMF. Accordingly, the provider computing system 104 may authenticate or authorize the computing device 108, select or query the PSMF repository 132 for the PSMF, and output the PSMF to the respective user computing device 108.

In some embodiments, at step 224, the provider computing system 104 may generate version data (e.g., version 0.1 for the generation of the PSMF) associated with the PSMF (and/or the PSMF data object of the PSMF). The version data may indicate the version of the PSMF and change (e.g., increment) as the PSMF is altered and/or approved.

Figure 3:
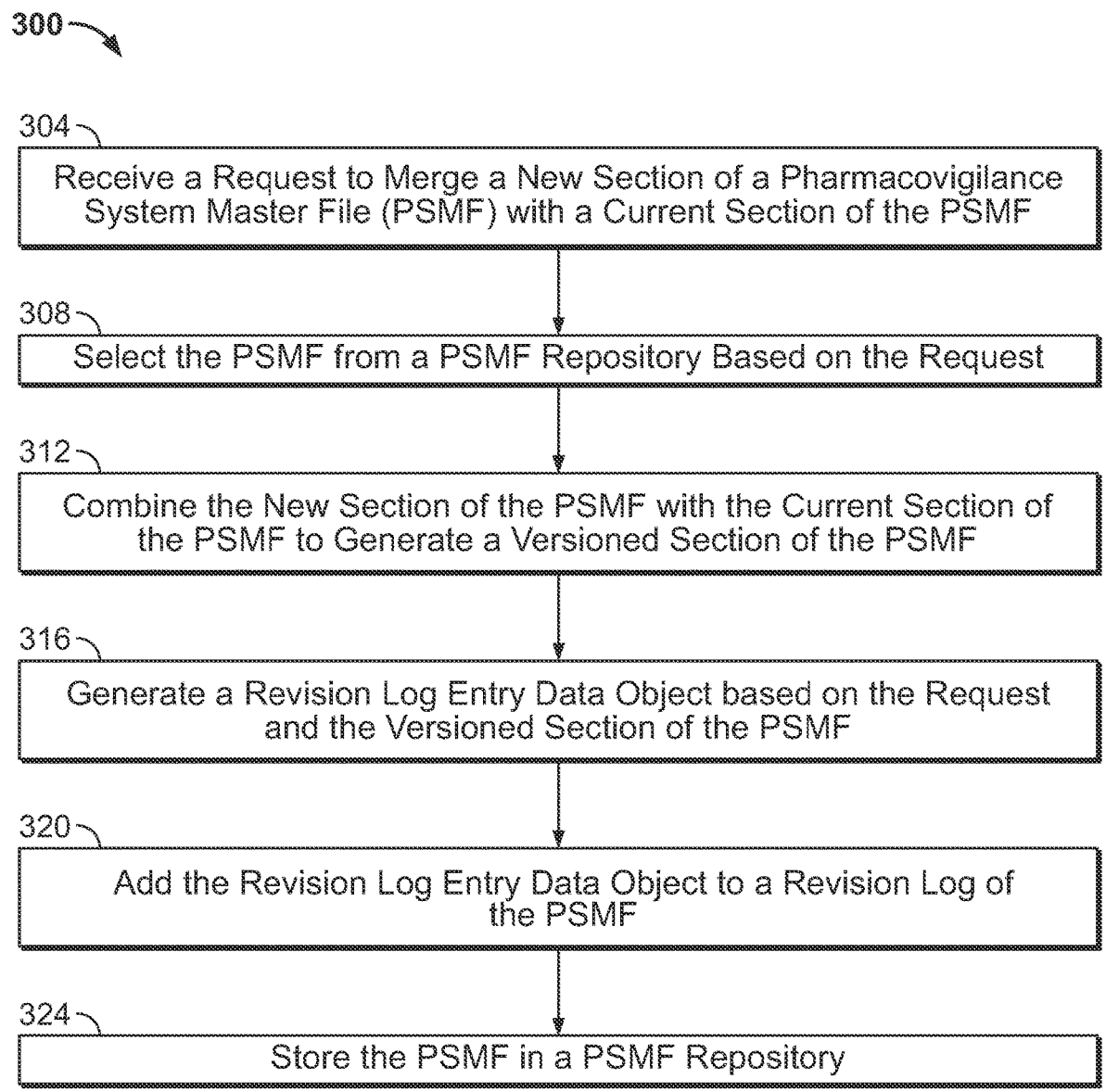
FIG. 3 is a flow diagram of a method for electronically tracking revisions in a PSMF, according to an example embodiment.

Referring now to FIG. 3, a method 300 of electronically tracking revisions in a PSMF is shown, according to an example embodiment. While overall different, it should be understood that any steps or discussion of the method 300 may be applied or included within the method 200, and vice versa. For example, the method 200 may include any of the steps 304-324, after or before any steps included in the method 200, and the method 300 may include any of the steps 204-224, after or before any of the steps included in the method 300. Method 300 can be carried out by the system of FIG. 1. More particularly, the method 300 can be carried out by the processing circuit 128 of the provider computing system 104 and through communication with the user computing device 108.

Method 300 commences at step 304 at which the provider computing system 104 receives a request to combine a new section of a PSMF with a current section of the PSMF. The request may include a text summary of changes or revisions from the current section to the new section. In some embodiments, the request to generate the PSMF may identify the PSMF itself or an associated medical product or company with which the PSMF is associated. In some embodiments, the request may further include a of combination that is to take place between the current section of the PSMF and the new section of the PSMF (e.g., overwrite, merge, etc.). The request may further include an electronic file associated with the new section of the PMSF. For instance, the user computing device 108 may provide the request with an electronic document (e.g., a Word document, a text document, etc.) or file representing the new section included therein.

In some embodiments, prior to step 304, the provider computing system 104 may receive a request to output the current section of the PSMF to the user computing device 108. In response, the provider computing system 104 may authorize the user computing device 108 and provide the current section of the PSMF to the user computing device 108. Further, the provider computing system 104 may modify the state of the current section of the PSMF to be a "checked-out" state, as will be described further herein with regard to FIG. 4.

Once the provider computing system 104 has receive the request, the method 300 proceeds to step 308 at which the provider computing system 104 selects or queries the PSMF from the PSMF repository 132 based on the request (e.g., based on the medical product of the request, based on the company of the request, based on the PSMF identified in the request, based on the current section identified in the request, etc.). In some embodiments (e.g., when the sections of the PSMF are stored separately from the PSMF), the provider computing system 104 may query or select the current section of the PSMF from the respective repository. In this regard, because the PSMF data object may include a reference pointer or link to the data object associated with the section of the PSMF, any changes made to the section of the PSMF will be included in the PSMF. In some embodiments, prior to selecting or querying the PSMF from the PSMF repository 132 (and proceeding with the method 300), the provider computing system 104 may authenticate and authorize the user computing device 108 that provided the request by confirming the user computing device 108 is permitted to make changes to the section of the PSMF (e.g., based on the permissions/list of usernames or emails received at step 204).

Once the provider computing system 104 has selected the PSMF (or the current section of the PSMF) from the PSMF repository 132, the method 300 proceeds to step 312 at which the provider computing system 104 combines the current section of the PSMF with the received new section of the PSMF to generate a versioned section of the PSMF. In some embodiments, the provider computing system 104 may combine the current section of the PSMF with the received new section of the PSMF based on the type of combination that is identified in the request. For instance, the request may identify the type of combination as overwrite. Accordingly at step 312, the provider computing system 104 may generate the versioned section generating new version data based on the previous version data (e.g., version 1.0 to version 1.1, version 1.0 to version 2.0, etc.) and using the new section as it was received (e.g., including the electronic document as it was received). In this regard, the versioned section may be the same as the new section. In another example, the request may identify the type of combination as merge. Accordingly at step 312, the provider computing system 104 may merge the current section and the new section (e.g., use portions of the current section and the new section) to generate the versioned section (as well as generating new version data based on the previous version data). In some embodiments, other types of combination (e.g., merge-in-part/overwrite-in-part, etc.) may be used when combining the current section and the new section. In this regard, the provider computing system 104 may combine portions of an electronic document of the current section with portions of the electronic document of the new section (e.g., keep the cover page of the current section but add the updated text of the new section, etc.).

Once the provider computing system 104 has combined the new section of the PSMF with the current section of the PSMF to generate the versioned section of the PSMF, the method 300 proceeds to step 316 at which the provider computing system 104 generates a revision log entry data object. As described herein, the request may include a text summary of revisions along with the new section of the PSMF. Accordingly, at step 316, the provider computing system 104 may generate the revision log entry data object, associated with the versioned section of the PSMF, that includes the respective text summary of revisions, the date and/or time the new section of the PSMF was received, a record of who made the changes (e.g., the name of the user who made the changes), the new version of the versioned section, and/or a reference pointer or link to the current version (e.g., a reference pointer to a data object associated with the section that holds the most up-to date version of the section, a version of the section, etc.) of the section.

Once the provider computing system 104 has generated the revision log entry data object, the method 300 proceeds to step 320 at which the provider computing system 104 adds the revision log entry data object to an electronic revision log of the PSMF. For instance, the provider computing system 104 may add a reference pointer or link (within the electronic revision log) to the revision log entry data object at step 320. In another example, the provider computing system 104 may add the data included within the revision log entry data object to the electronic revision log. In some embodiments, prior to step 320, the provider computing system 104 may select or query the electronic revision log from the electronic revision log database 134. In some embodiments, once the provider computing system 104 adds the revision log entry data object to the electronic revision log, the provider computing system 104 may generate new version data based on the previous version data (e.g., version 0.1 to version 0.2, version 1.0 to version 2.0, etc.) and add the new version data to the electronic revision log (e.g., to the electronic revision log data object).

In some embodiments, after step 320, the provider computing system 104 may generate an electronic revision log document. The electronic revision log document may be a PDF, HTML/HTMLS, XLS, TXT, or DOC/DOCX file that includes each of the revision log entries of the revision log within a single electronic document. In another example, as described previously herein, the provider computing system 104 may generate the electronic revision log document by combining or compiling at least a portion of the revision log entry data objects (the text summary, the date, the user, the section title or name, etc.) of each revision log into a single electronic document. To do so, the provider computing system 104 may compile each revision log entry data object into the same file format in the correct order based on the date or time of the revision log entry data object (e.g., an entry from the year 2001 is before an entry from the year 2002, etc.). In some embodiments, the electronic revision log document may be stored with the electronic revision log in the electronic revision log repository 134.

Once the provider computing system 104 has added the revision log entry data object to the electronic revision log, the method 300 proceeds to step 324 at which the provider computing system 104 stores the PSMF within the PSMF repository 132. In some embodiments, the PSMF may be stored separately from the sections of the PSMF and/or the electronic revision log. For instance, the PSMF may be stored within the PSMF repository 132, the electronic revision log may be stored within the electronic revision log repository 134, and the other sections of the PSMF may be stored in separate repositories (as described herein).

In some embodiments, before step 324, the provider computing system 104 may generate an electronic PSMF document. The electronic PSMF document may be a PDF, HTML/HTMLS, XLS, TXT, or DOC/DOCX file that includes each of the sections of the PSMF and the electronic revision log within a single electronic document. To do so, the provider computing system 104 may generate a table of contents representative of each section and the electronic revision log and then compile each section of the PSMF into the same file format in the correct order displayed (e.g., section 1 before section 2, etc.). In some embodiments, the electronic PSMF document may be stored with the PSMF in the PSMF repository 132 at step 324. In some embodiments, after step 324, the provider computing system 104 may receive a request to output the PSMF. Accordingly, the provider computing system 104 may authenticate or authorize the computing device 108, select or query the PSMF repository 132 for the PSMF, and output the PSMF to the respective user computing device 108.

In some embodiments, step 304-324 may be repeated for a second request. For instance, the provider computing system 104 may proceed through the method 300, in response to receiving a first request to merge a first new section of the PSMF with a first current section (e.g., Annex A) of the PSMF. Then, in response to receiving a second request associated with a second current section of the PMSF (e.g., Annex B), the provider computing system 104 may repeat each step of the method 300.

Referring now to FIGS. 4-5, user interfaces shown and displayed to the user of the user computing device 108 during the method 200 and/or the method 300 are shown, according to example embodiments. As described herein, the user interfaces of FIGS. 4-5 may be one or more of web interfaces generated by the provider computing system 104 and rendered by the user computing device 108 as part of a web application, or graphical user interfaces downloaded and generated by the user computing device 108 as part of a software application (e.g., a mobile application, etc.). Further, the user interfaces shown on FIGS. 4-5 allow for communication between the user and the provider computing system 104 via the user computing device 108 (specifically via the I/O circuit 162). Through interaction with the various user interfaces, the user may provide user input, feedback, and other data requested by the provider computing system 104. In this regard, it should be understood that each interaction described herein by the user with the user interfaces of FIGS. 4-5 may be provided to the user computing device 108 and then transmitted to the provider computing system 104 and that each action described herein as occurring to the user and/or the user computing device 108 (e.g., navigating to a certain page, generating a popup, etc.) may be performed by the provider computing system 104.

Referring now to FIG. 4, a PSMF page 400, which can be displayed on a display of the I/O circuit 162 of the one or more of the user computing devices 108, is shown. In general, the PSMF page 400 provides the respective user computing device 108 with an interface to view and manage the PSMF (and associated sections) described herein. For example, via the PSMF page 400, the user may select and view one or more sections of the PSMF; select and request one or more sections of the PSMF; and provide new sections of the PSMF to be merged with current sections of the PSMF. In this regard, the provider computing system 104 may provide the PSMF and associated sections to the respective user computing device 108 to enable display of the PSMF page 400 on the display of the I/O circuit 162. As shown, the PSMF page 400 includes a cover page representation 404, a table of contents representation 406, a core drop-down box 408, an annexes drop-down box 410, a signature page representation 438, Annex A-I drop-down boxes 412-430, a revision control drop-down box 433, and a revision log representation 434.

Each of the representations (e.g., the cover page representation 404, the table of contents representation 406, the revision log representation 434, the signature page representation 438) may be selectable buttons that represent a current section (e.g., an electronic document of the current section) of the PSMF and that, when selected, provide a request to the provider computing system 104 to provide the current section to the user computing device 108. For instance, the revision log representation 434 may represent the electronic revision log (e.g., the electronic document associated with the revision log). Then, when the revision log representation 434 is selected (e.g., clicked, double-clicked, clicked and then another button is clicked, etc.), the user computing device 108 may provide a request to the provider computing system 104 for the revision log of the PSMF. In response, the provider computing system 104 may authorize the request (e.g., confirm the user of the user computing device 108 has access to the revision log) and provide the electronic revision log document to the user computing device 108. Further, the versions in the name of the representations (e.g., "v1.0," "v0.1," etc.) may represent the version data of the respective section.

In some embodiments, when the provider computing system 104 receives a request to provide the current section represented by the representation and then provides the current section, the provider computing system 104 may modify the current section of the PSMF to a "checked-out" state. In the "checked-out" state, other user computing devices may have to request access from the user computing device 108, via the provider computing system 104, to receive the current section of the PSMF. Then, when the user computing device 108 indicates the current section of the PSMF is "checked-in" (e.g., by sending an indication of such) or provides a new section of the PSMF to override the current section of the PSMF, the provider computing system 104 may modify the section of the PSMF to a "checked-in" state, in which the section of the PSMF can be requested and provided as described herein.

In one example, to generate a new section of the cover page, the user of the user computing device 108 may select the cover page representation 404, be authenticated, and receive the cover page electronic document. The provider computing system 104 may modify the cover page section to the checked-out state. The user of the user computing device 108 may then modify the cover page electronic document (thereby creating a new cover page electronic document). The user computing device 108 may then provide the new cover page section (e.g., the new cover page electronic document) in a request to combine the new cover page with the current cover page to the provider computing system 104. As a result, the provider computing system 104 may proceed with the method 300, as described herein, and add the new cover page to the PSMF (as well as change the cover page section of the PSMF to the checked-in state.

Each of the drop-down boxes (e.g., the core drop-down box 408, the core drop-down boxes (not shown), the annexes drop-down box 410, the Annex A-I drop-down boxes 412-430 and the revision control drop-down box 433) may be drop-down boxes that, when selected, drop-down multiple selectable options. For instance, the Annex A drop-down box 412, when selected, may drop down the portions of the Annex A section described herein. For instance, the Annex A drop-down box 412 may display a selectable Annex A representation. In this regard, the drop-down boxes provide for a form of organization of the PSMF.

Referring now to FIG. 5, a revision log page 500, which can be displayed on a display of the I/O circuit 162 of the one or more of the user computing devices 108, is shown. In general, the revision log page 500 provides the respective user computing device 108 with an interface to view and manage the revision log (and associated revision log entry data objects) described herein. For example, via the revision log page 500, the user may select, create, and view one or more revision log entries of a specific section of the PSMF. In this regard, the provider computing system 104 may provide the revision log and the associated revision log data objects to the respective user computing device 108 to enable display of the revision log page 500 on the display of the I/O circuit 162. As shown, the revision log page 500 includes a details or overview section 504 and a revision log entries section 520.

The revision log details section 504 provides the user of the respective user computing device 108 with an interface to review and manage the data of the revision log and includes a name field 506, a status field 508, a created by field 510, a created date field 512, a last modified by field 514, a last modified date 516, and a related document or section field 518. It should be understood that each of the fields 504-518 may be included in or a part of the data of the revision log (i.e., revision log data) described herein.

The name field 506 is a selectable and/or editable text field through which the user of the respective user computing device 108 can edit the name of the electronic revision log which may then be sent by the respective user computing device 108 to the provider computing system 104 for storage. Similarly, the status field 508 is a selectable and/or editable text field through which the user of the respective user computing device 108 can set the status of the revision log (e.g., checked-in, checked-out, active, inactive) which may then be sent by the respective user computing device 108 to the provider computing system 104 for storage.

The created by field 510 is a text field that includes the name of the user who created the electronic revision log. If the electronic revision log was created by the provider computing system 104, the created by field 510 may include the name "system". Whereas, the last modified field 514 is a text field that includes the name of the user who last modified or edited the electronic revision log. If the electronic revision log was last modified by the provider computing system 104, the last modified field 514 may include the name "system". The created date field 512 is a text field that includes the date and/or time the electronic revision log was created. Whereas, the last modified date field 516 is a text field that includes the date and/or the time the electronic revision log was last modified or edited.

The related document or section field 518 is a selectable field that includes the section of the PSMF associated with the electronic revision log. In some embodiments, the related section field 518 is a selectable link that, when selected, navigates the user of the user computing device 108 to a section page (not shown) associated with the specific related section.

The revision log entries section 520 provides the user of the respective user computing device 108 with an interface to review and manage the revision log entry data objects of the respective electronic revision log and includes multiple revision log entry representations 522.

Each revision log entry representation 522 represents a specific revision log entry data object, and includes an entry name field 524, an entry date field 526, a user making changes field 528, and a summary of changes field 530. It should be understood that each of the fields 524-530 may be included in or a part of the revision log entry data object described herein.

The name field 524 is a selectable and/or editable text field through which the user of the respective user computing device 108 can edit the name of the electronic revision log entry data object associated with the revision log entry representation 522 which may then be sent by the respective user computing device 108 to the provider computing system 104 for storage. Similarly, the date field 526 is a text field that includes the date and/or time the request (of steps 204 and 304) was received, as described herein with regard to the methods 200 and 300. Likewise, the person making changes field 528 is a text field that includes the name of the user who made changes to the current section of the PSMF, as described with regard to the methods 200 and 300. Further, the summary of changes field 530 is a text field that includes the text summary of changes included in the request (of steps 204 and 304), as described herein with regard to the methods 200 and 300.

Referring now to FIG. 6, an electronic PSMF document 600 is shown according to an example embodiment. The electronic PSMF document 600 is shown to include revision log section 605 with multiple revision log entry portions 610. The electronic PSMF document 600 is further shown to include multiple bookmarks 640. While the electronic PSMF document 600 is shown as a PDF file, the electronic PSMF document 600 may be other file types including HTML/HTMLS, XLS, TXT, and/or or DOC/DOCX file types. The bookmarks 640 are selectable buttons that, when selected, navigate the user of the user computing device 108 to the section represented by the specific bookmark. For instance, the "Section 3" bookmark 640, when selected, will automatically navigate the user of the user computing device 108 to Section 3 of the electronic PSMF document 600.

Referring now to FIG. 7, an electronic revision log document 700 is shown according to an example embodiment. The electronic revision log document 700 is shown to include multiple revision log entry portions 710. For instance, each revision log entry portion 710 is shown to include at least a portion of the revision log entry data object (e.g., the narrative or text summary of the revision log entry data object, the person or user record of the user who made the changes/entry of the revision log entry data object, the section or document name of the parent revision log, and/or the date on which the entry was made). Further, as shown, the revision log entry portions 710 are compiled or listed by date such that the oldest date is proximate the top of the electronic revision log document 700 and the newest date is proximate the bottom of the electronic revision log document 710. While the electronic revision log document 700 is shown as a XLS file, the electronic revision log document 700 may be other file types including HTML/HTMLS, PDF, TXT, and/or or DOC/DOCX file types.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112 (f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FPGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, the circuits of the processing circuit described herein may be distributed across one or more locations (e.g., each as part of one or more remote servers).

An example system for implementing the overall system or portions of the embodiments might include a general-purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general-purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that the term "field," as described herein may include any form of an input field through which the user interfaces shown and described may receive input from a user of a computing device. For instance, the term "field" may include a text field, a drop-down box and selectable options, a lookup box, a search bar, an icon, one or more checkboxes, one or more radio buttons, a button, a toggle, a date field, a slider, and the like. Further, each "field" may include and/or receive data that is associated with a data object as described herein.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for revision control of an electronic file comprising:
   receiving, by a provider computing system, a request to merge a new section of the electronic file with a current section of the electronic file, the request including an electronic document associated with the new section of the electronic file;
   selecting, by the provider computing system, the electronic file from a repository of the provider computing system based on the request, wherein the electronic file includes a plurality of sections including the current section, and wherein each section of the plurality of sections comprises a revision log including at least one revision log entry data object,
   wherein each revision log entry data object includes a date;

generating, by the provider computing system, a versioned section of the electronic file based on the request, the versioned section including the electronic document of the request and the revision log of the current section;

generating, by the provider computing system, a revision log entry data object based on the request and the versioned section of the electronic file, the revision log entry data object including a new date;

adding, by the provider computing system, the revision log entry data object to the revision log of the versioned section;

generating, by the provider computing system, an electronic revision log document, wherein the electronic revision log document is generated as a specific file type, wherein the specific file type is one of: a text file, a spreadsheet file, or a Comma-Separated Value (CSV) file, and wherein generating the electronic revision log document files comprises:

compiling, by the provider computing system, at least a portion of each revision log entry data object of each revision log of each section of the plurality of sections by date; and generating, by the provider computing system, the electronic revision log document by transforming the compiled at least a portion of each revision log entry data object into the specific file type of the electronic revision log document;

adding, by the provider computing system, the electronic revision log document to the electronic file; and storing, by the provider computing system, the electronic file in the repository.

2. The method of claim 1, wherein the request identifies an overwrite type of combination, and wherein the provider computing system generates the versioned section including the electronic document based on the overwrite type of combination of the request.

3. The method of claim 1, wherein the request is a first request, wherein the new section is a first new section, wherein the current section is a first current section, wherein the versioned section is a first versioned section, wherein the revision log entry data object is a first revision log entry data object, wherein the revision log is a first revision log, and wherein the method further comprises:

receiving, by a provider computing system, a second request to merge a second new section of the electronic file with a second current section of the electronic file, the request including a second electronic document associated with the second new section of the electronic file;

generating, by the provider computing system, a second versioned section of the electronic file based on the request, the second versioned section including the second electronic document of the request and the revision log of the second current section;

generating, by the provider computing system, a second revision log entry data object based on the second request and the second versioned section of the electronic file, the second revision log entry data object including a second new date; and adding, by the provider computing system, the second revision log entry data object to the revision log of the second versioned section.

4. The method of claim 1, wherein the current section includes a current section data object, the current section data object including the revision log of the current section and a current section electronic file, and wherein the versioned section includes a versioned section data object including the electronic document and the revision log of the current section.

5. The method of claim 4, wherein the current section data object further includes current version information, and wherein generating the versioned section comprises:

generating, by the provider computing system, new version information based on the current version information of the current section data object; and generating, by the provider computing system, the versioned section data object including the electronic document, the new version information, and the revision log of the current section.

6. The method of claim 4, wherein the revision log of the versioned section includes a revision log data object, and wherein adding the revision log entry data object to the revision log comprises:

adding, by the provider computing system, a reference pointer to the revision log entry data object in the revision log data object.

7. The method of claim 1, wherein each revision log entry data object further includes a user record and a text summary.

8. The method of claim 1, wherein the provider computing system compiles at least a portion of each revision log entry data object by date such that at least a portion of a first revision log entry data object with a first date is located above at least a portion of a second revision log entry data object with a second date, wherein the second date is after the first date.

9. The method of claim 1, wherein each revision log includes at least one revision log entry data object that is an initial entry generated by the provider computing system in response to generating each section of the plurality of sections.

10. The method of claim 1, wherein the electronic file is a Pharmacovigilance Safety Master File (PMSF) binder including a link to each of the plurality of sections.

11. A method for revision control of an electronic file comprising:

receiving, by a provider computing system, a request to merge a new section of the electronic file with a current section of the electronic file, the request including an electronic document associated with the new section of the electronic file;

selecting, by the provider computing system, the electronic file from a repository of the provider computing system based on the request, wherein the electronic file includes the current section, and wherein the current section comprises a revision log including a first revision log entry data object, wherein the first revision log entry data object includes a date;

generating, by the provider computing system, a versioned section of the electronic file based on the request, the versioned section including the electronic document of the request and the revision log of the current section;

generating, by the provider computing system, a second revision log entry data object based on the request and the versioned section of the electronic file, the second revision log entry data object including a new date;

adding, by the provider computing system, the second revision log entry data object to the revision log of the versioned section;

generating, by the provider computing system, an electronic revision log document, wherein the electronic revision log document is generated as a specific file type, wherein the specific file type is one of: a text file, a spreadsheet file, or a Comma-Separated Value (CSV) file, and wherein generating the electronic revision log document files comprises:
  compiling, by the provider computing system, at least a portion of the first revision log entry data object and the second revision log entry data object by date;
  generating, by the provider computing system, the electronic revision log document by transforming the compiled at least a portion of the first revision log entry data object and the second revision log entry data object into the specific file type of the electronic revision log document;
  adding, by the provider computing system, the electronic revision log document to the electronic file; and
  storing, by the provider computing system, the electronic file in the repository.

12. The method of claim 11, wherein the request is a first request, wherein the new section is a first new section, wherein the current section is a first current section, wherein the versioned section is a first versioned section, wherein the revision log is a first revision log, and wherein the method further comprises:
  receiving, by a provider computing system, a second request to merge a second new section of the electronic file with a second current section of the electronic file, the request including a second electronic document associated with the second new section of the electronic file;
  generating, by the provider computing system, a second versioned section of the electronic file based on the request, the second versioned section including the second electronic document of the request and a revision log of the second current section;
  generating, by the provider computing system, a third revision log entry data object based on the second request and the second versioned section of the electronic file, the third revision log entry data object including a second new date; and
  adding, by the provider computing system, the third revision log entry data object to the revision log of the second versioned section,
  wherein the provider computing system generates the electronic revision log document by compiling at least a portion of the first revision log entry data object, the second revision log entry data object, and the third revision log entry data object by date.

13. The method of claim 11, wherein the current section includes a current section data object, the current section including the revision log of the current section and a current section electronic file, and wherein the versioned section includes a versioned section data object including the electronic document and the revision log of the current section.

14. The method of claim 13, wherein the current section data object further includes current version information, and wherein generating the versioned section comprises:
  generating, by the provider computing system, new version information based on the current version information of the current section data object; and
  generating, by the provider computing system, the versioned section data object including the electronic document, the new version information, and the revision log of the current section.

15. The method of claim 13, wherein the revision log includes a revision log data object, and wherein adding the second revision log entry data object to the revision log comprises:
  adding, by the provider computing system, a reference pointer to the second revision log entry data object in the revision log data object.

16. The method of claim 11, wherein the first revision log entry data object includes a first user record and a first text summary, wherein the second revision log entry data object includes a second user record and a second text summary.

17. The method of claim 11, wherein the provider computing system compiles at least a portion of the first revision log entry data object and the second revision log entry data object by date such that at least a portion of the first revision log entry data object is located above at least a portion of the second revision log entry data object in response to the date of the first revision log entry data object being before the new date of the second revision log entry data object.

18. The method of claim 11, wherein the first revision log entry data object is an initial entry generated by the provider computing system in response to generating the current section.

19. The method of claim 11, wherein the electronic file is a Pharmacovigilance Safety Master File (PMSF) binder including a link to the versioned section.

20. The method of claim 11, wherein the request identifies an overwrite type of combination, and wherein the provider computing system generates the versioned section including the electronic document based on the overwrite type of combination of the request.

* * * * *